United States Patent [19]

Cardinaux et al.

[11] Patent Number: 4,758,550
[45] Date of Patent: Jul. 19, 1988

[54] CALCITONIN DERIVATIVES

[75] Inventors: Francois Cardinaux, Seewen; Janos Pless, Basel, both of Switzerland; Robert H. Buck, Rheinfelden, Fed. Rep. of Germany

[73] Assignee: Sandoz Ltd., Basel, Switzerland

[21] Appl. No.: 937,580

[22] Filed: Dec. 3, 1986

[30] Foreign Application Priority Data

Dec. 4, 1985 [DE] Fed. Rep. of Germany ....... 3542859
May 2, 1986 [DE] Fed. Rep. of Germany ....... 3614784

[51] Int. Cl.$^4$ .......................... A61K 37/24; C07K 7/36
[52] U.S. Cl. ....................................... 514/12; 514/808; 530/307
[58] Field of Search ................... 530/307; 514/12, 808

[56] References Cited

U.S. PATENT DOCUMENTS 4,622,386 11/1986 Orlowski et al. .................. 530/307
4,658,014 4/1987 Kempe ............................... 530/307
4,663,309 5/1987 Kaiser et al. ....................... 530/307

*Primary Examiner*—Delbert R. Phillips
*Attorney, Agent, or Firm*—Gerald D. Sharkin; Robert S. Honor; Thomas O. McGovern

[57] ABSTRACT

A compound of formula I

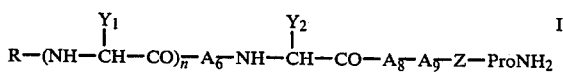

wherein

R is H or R'CO wherein R'CO is an acyl radical of a carboxylic acid, $Y_1$ is the radical linked to an alpha carbon atom an α-amino acid, $Y_2$ is the radical linked to an alpha carbon atom of an α-amino acid,

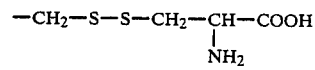

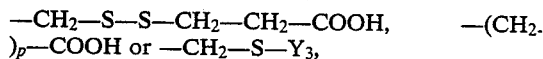

$Y_3$ is $(C_{1-4})$alkyl or benzyl optionally substituted by methyl or methoxy, or $CH_3CO-NH-CH_2-$, n is 1 to 4, $A_6$ is Thr or D-Thr, p is 3 to 5, $A_8$ is the aminoacyl radical of a neutral, lipophilic L-α-aminoacid, $A_9$ is the aminoacyl radical of a neutral, lipophilic L- or D-α-aminoacid, Z is a polypeptide radical corresponding to the polypeptide radical in positions 10 to 31 of a natural calcitonin or a derivative or analogue thereof having a hypocalcemic effect, wherein, when there is more than one $Y_1$ radical, these are the same or different, and with the exception of radical $A_8$, all amino acid radicals may have the L- or D-configuration, with the proviso that when $Y_2$ is $-CH_2-SH$ and n is 4, then the N terminal aminoacyl radical is other than H—CyS, have calcitonin like activity.

14 Claims, No Drawings

CALCITONIN DERIVATIVES

This invention relates to calcitonin derivatives.

The present invention provides a compound of formula I

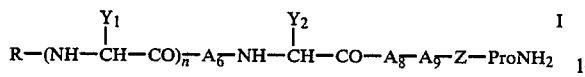

wherein

R is H or R'CO wherein R'CO is an acyl radical of a carboxylic acid, $Y_1$ is the radical linked to an alpha carbon atom of an α-amino acid, $Y_2$ is the radical linked to an alpha carbon atom of an α-amino acid,

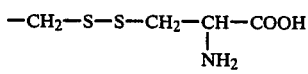

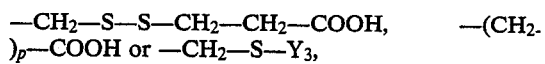

$Y_3$ is $(C_{1-4})$alkyl, or benzyl optionally substituted by methyl or methoxy,
or $CH_3CO-NH-CH_2-$, n is 1 to 4, $A_6$ is Thr or D-Thr, p is 3 to 5.

$A_8$ is the aminoacyl radical of a neutral, lipophilic L-α-aminoacid, $A_9$ is the aminoacyl radical of a neutral, lipophilic L- or D-α-aminoacid, Z is a polypeptide radical corresponding to the polypeptide radical in positions 10 to 31 of a natural calcitonin or a derivative or analogue thereof having a hypocalcemic effect, wherein, when there is more than one $Y_1$ radical, these are the same or different, and with the exception of radical $A_8$, all amino acid radicals may, independently, have the L- or D-configuration, with the proviso that when $Y_2$ is $-CH_2SH$ and n is 4, then the N terminal aminoacyl radical is other than H—CyS.

The compounds may be in free form, in salt form or in complex form. In each of these forms, it may be hydrated.

Z in formula I is understood to be those peptide radicals which are present in positions 10 to 31 in the various known calcitonins, e.g. in human, salmon, eel, cattle, sheep, chicken, rat or pig calcitonin, as well as in the derivatives and analogs of these calcitonins having hypocalcemic activity, e.g. as described in the tests hereinafter or having calcitonin-like activity. The derivatives and analogs of these calcitonins are understood to be in particular natural calcitonins, wherein one or several amino acid radicals are replaced by one or several other aminoacid radicals, or the S-S-bridge is replaced by a alkylene bridge, or wherein one or several aminoacids are omitted. The peptide radical Z is conveniently 22 amino acids in length, but by the omission of one or several amino acid residues (desaminoacyl derivatives) may contain fewer amino acid radicals.

Preferred compounds of formula I are those wherein Z is (a) Gly-Thr-Tyr-Thr-Gln-Asp-Phe-Asn-Lys-Phe-His-Thr-Phe-Pro-Gln-Thr-Ala-Ile-Gly-Val-Gly-Ala (b) Gly-Lys-Leu-Ser-Gln-Glu-Leu-His-Lys-Leu-Gln-Thr-Tyr-Pro-Arg-Thr-Asp-Val-Gly-Ala-Gly-Thr (c) Gly-Lys-Leu-Ser-Gln-Glu-Leu-His-Lys-Leu-Gln-Thr-Tyr-Pro-Arg-Thr-Asn-Thr-Gly-Ser-Gly-Thr Special preference is given to compounds of formula I, wherein Z has the definition given above under (b) or (c), more especially (c), R'CO is conveniently an acyl radical of an aliphatic, cycloaliphatic, aromatic or heterocyclic carboxylic acid, R' is preferably:

(a') a $(C_{1-17})$alkyl radical, especially a $(C_{3-9})$alkyl radical, (Preferably it is saturated).

(b') $(C_{5-7})$cycloalkyl or $(C_{5-7})$cycloalkyl$(C_{1-2})$alkyl radicals, (c') Adamantyl, adamantylmethyl or adamantylethyl, or (d') phenyl, benzyl or phenylethyl.

The alkyl, cycloalkyl or phenyl radicals may be substituted by e.g. halogen, (e.g., of atomic number from 9 to 35), nitro, OH, alkoxy etc. Preferably only one substituent is present.

The radical R'CO may be for example a desamino radical of a natural α-aminoacid.

For R' definitions (a'), (b') and (c') are preferred.

The α-amino acid corresponding to $Y_1$ and $Y_2$ is preferably a natural amino acid. Alternatively the α-amino acid may be, e.g. 3-cyclohexylalanine or α-aminoisobutyric acid.

When n is 4, (a") the N terminal acylamino radical (corresponding to the second aminoacid radical in the natural calcitonin) is preferably, Ser, Gly or Ala, (b") the second aminoacyl radical (corresponding to the third aminoacid radical in the natural calcitonin) is preferably Asn or Ser, (c") the third aminoacyl radical (corresponding to the fourth aminoacid radical in the natural calcitonin is preferably Leu, Asn, Ser, Phe, D-Leu or the radical of cyclohexylalanine, (d") the fourth aminoacyl radical (corresponding to the fifth aminoacid radical in the natural calcitonin is preferably Ser or Ala.

When n is 3, the N-terminal, second and third aminoacyl radicals preferably have the preferences (b"), (c") and (d") respectively.

When n is 2, the N-terminal and second aminoacyl radicals preferably have the preference (c") and (d") respectively.

When n is 1 the N-terminal amino acyl radical is preferably Ser or Ala.

$A_6$ is preferably Thr.

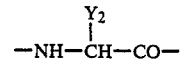

is preferably Cys, a derivative of Cysteine as defined above for $Y_2$ or a neutral lipophilic α-aminoacyl radical, especially Ala, more preferably a neutral lipophilic α-aminoacyl radical, especially Ala.

The N-terminal acyl radical refers to R or R—(NH—CH($Y_1$)CO).

$A_8$ is preferably an aminoacyl radical of a neutral, lipophilic alpha-amino acid, especially Val or Gly.

$A_9$ is preferably an aminoacyl radical of a neutral, lipophilic alphaamino acid, especially Leu or Phe.

n is preferably 2-; R is H or R'CO or especially n is 1 and R is R'CO.

Preferably all amino acid radicals have the L-configuration.

A group of compounds is of formula Ip

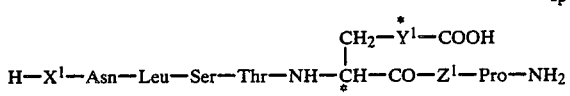

wherein
X¹ denotes Gly or Ser
Y¹ denotes (CH₂)₄ or

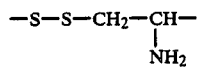

wherein the latter radical is attached through the terminal S-atom to the adjacent-CH₂- group in formula Ip, and Z¹ denotes a polypeptide radical which is made up of 24 amino acids, and which corresponds to that in positions 8 to 31 of a natural calcitonin or of a derivative or analog thereof having hypocalcemic activity, and wherein all the amino acid radicals, including those in positions marked *, have the L-configuration.

Preferably X¹ is Ser; or Y¹ denotes

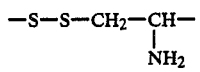

or Z¹ denotes Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr.

Also preferred are
(a) X=Gly
Z=Met-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala
(b) X=Ser
Z=Val-Leu-Gly-Lys-Leu-Ser-Gln-Glu-Leu-His-Lys-Leu-Gln-Thr-Tyr-Pro-Arg-Thr-Asp-Val-Gly-Ala-Gly-Thr.

Another group of compounds has formula Ipa

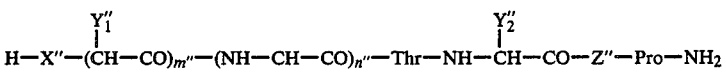

wherein
X″ denotes NH or a bond, but, if m″=0, it only denotes a bond,
Y₁″ denotes the radical which is linked to the α-C-atom of a natural amino acid,
Y₂″ denotes the radical which is linked to the α-C-atom of a natural α-amino acid, or it denotes

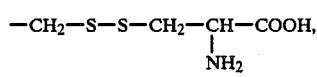

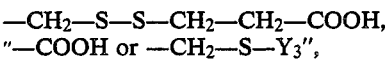 —(CH₂)ₚ″—COOH or —CH₂—S—Y₃″,
Y₃″ denotes alkyl with 1 to 4 C-atoms,
m″ denotes 0 or 1,
n″ denotes 0 to 3,
p″ denotes 3 to 5, and
Z″ denotes the polypeptide radical which is made up of 24 amino acids, and which corresponds to positions 8 to 31 of a natural calcitonin or of a derivative or analog thereof having hypocalcemic activity,
whereby the 1 to 4 Y₁″ radicals in formula Ipa may have the same or different definitions, and all the amino acids in formula I may independently have the L- or D-configuration.

A group of compounds has Z″=
(a) Met-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala
(b) Val-Leu-Gly-Lys-Leu-Ser-Gln-Glu-Leu-His-Lys-Leu-Gln-Thr-Tyr-Pro-Arg-Thr-Asp-Val-Gly-Ala-Gly-Thr, or
(c) Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr.

In formula Ipa, the radical

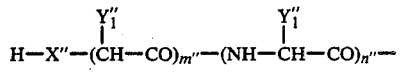

preferably denotes

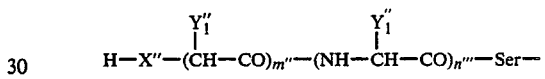

wherein n‴ denotes 0 to 2, or

wherein n″″ denotes 0 or 1, and the radicals Y₁″ preferably denote CH₂OH, (CH₃)₂CH—CH₂ or CH₂—CONH₂.

The free form of the compound of formula I may be a free base form or e.g. when an acid group is present a free acidic form.

The polypeptides of the invention may exist in salt form or in the form of complexes thereof. Acid addition salts may be formed with e.g. organic acids, including polymeric acids and inorganic acids. Such acid addition salt forms include e.g. the hydrochlorides and acetates. By complexes are to be understood compounds of known type, formed from compounds of formula I on addition of inorganic substances, e.g. inorganic salts or hydroxides such as Ca- and Zn-salts, and/or on addition of polymeric organic substances.

The present invention also provides a process for the production of the compounds of formula I. These compounds may be produced e.g. by methods known in the art of peptide chemistry or by obvious chemical equivalents thereof, for example, by a process comprising:
(a) removing at least one protecting group from a protected polypeptide having the sequence indicated in formula I,
(b) linking together by an amide bond two peptide units, each of which contains at least one amino acid as defined in formula I or a derivative thereof in protected or unprotected form, the peptide units being such that a protected or unprotected polypeptide having the sequence indicated in formula I, is obtained and, if necessary, carrying out process step (a); for the production of a compound of formula I having a terminal group R'CO—, reacting a protected or unprotected peptide having the sequence indicated in formula I with an acid of formula R'COOH or a reactive acid derivative thereof, and if necessary, carrying out process step (a);

(d) for the production of compounds of formula I, wherein $Y_2$ is $$-CH_2-S-S-CH_2-\underset{\underset{NH_2}{|}}{CH}-COOH$$

or $-CH_2-S-S-CH_2-CH_2-COOH$ either reacting a compound of formula II $$R + NH-\underset{\underset{Y_1}{|}}{CH}-CO \xrightarrow{}_n A_6 - NH - \underset{\underset{CH_2-SH}{|}}{CH} - CO - A_8 - A_9 - Z - ProNH_2 \qquad II$$

in protected or unprotected form, with a compound of formula III $$R_2-\underset{\underset{CH_2-S-R_1}{|}}{CH}-COR_3 \qquad III$$

wherein $R_1$ signifies a group which facilitates the formation of an -S-S-bridge with the S-atom of the $CH_2SH-$ group in the polypeptide of formula II, $R_2$ is hydrogen, amino, or a protected amino group, and $R_3$ signifies OH or a protecting group for the carboxyl group, or reaction a compound of formula IV $$R + NH-\underset{\underset{Y_1}{|}}{CH}-CO \xrightarrow{}_n A_6 - NH - \underset{\underset{CH_2-SR_1}{|}}{CH} - CO - A_8 - A_9 - Z - ProNH_2 \qquad IV$$

in protected or unprotected form, wherein $R_1$ is defined as above, with a compound of formula V $$R_2-\underset{\underset{CH_2-SH}{|}}{CH}-COR_3 \qquad V$$

and then optionally effecting stage (a) of the process, and where required converting the polypeptide thus obtained into free form, acid addition salt form or complex form.

The above process may for example be carried out analogously to the processes described in the accompanying examples. Insofar as the production of the starting materials is not particularly described, the compounds are known or may be produced and purified in accordance with methods known in the art.

The final compounds of formula I may also be purified in conventional manner, so they contain less than 5% or less than other polypeptide by-products.

The polypeptides used as starting products for processes (a) and (b) may similarly be produced in known manner in solution or by the solid phase process.

Production of peptide units which contain a $-CH_2-S-S-CH_2-CH_2-COOH$ or $CH_2-S-S-CH_2CH(NH_2)-COOH$ radical group as the $Y_2$-radical may be effected analogously to the above-mentioned process (d).

In this process (d), compounds of formula III or IV may be used, in which $R_1$ denotes the known radicals which react with mercaptans whilst forming a S-S-bond. $R_1$ especially denotes S-alkyl, S-COOalkyl, $$-S-\underset{}{\bigcirc}-NO_2 \quad ,$$

or $-S-SO_3-$. In these radicals, alkyl especially denotes $(C_{1-4})$alkyl. The introduction of these radicals into the compounds having free SH-groups take place analogously to methods which are known in sulphur chemistry.

In the following examples all temperatures are in °C. and $[\alpha]_D^{20}$—values are uncorrected. The following abbreviations are employed:

Aib = α-aminoisobutyric acid residue $$(CH_3)_2-C\underset{\diagdown NH-}{\overset{\diagup CO-}{}}$$

Boc = tert.-butoxycarbonyl
$Bu^t$ = tert. butyl
Fmoc = 9-fluorenylmethoxycarbonyl
Scm = methoxycarbonylsulphenyl
Trt = trityl
Asu = α-aminosuberinic acid
Cys (Me) = S-methylcysteine
Acm = acetoamidomethyl
Cha = 3-cyclohexylalanine residue $$C_6H_{11}-CH_2-CH\underset{\diagdown NH-}{\overset{\diagup CO-}{}}$$

DMF = Dimethylformamide
DCM = dichloromethane

All peptides are obtained as a polyacetate polyhydrate except where otherwise stated with a peptide content of from 70 to 90%. The polypeptides contain less than 5% of other peptides by HPLC-analysis.

"F" as used hereinafter refers to the proportion of polypeptides (=peptide content) in the preparations obtained (F=1 corresponds to 100 percent), the difference to 100% is made of acetic acid and water.

EXAMPLE 1

H—Leu—Ser—Thr—Cys(H—Cys—OH)—Val—Leu—Gly—

—Lys—Leu—Ser—Gln—Glu—Leu—His—Lys—Leu—Gln—

—Thr—Tyr—Pro—Arg—Thr—Asn—Thr—Gly—Ser—Gly—

—Thr—Pro—NH$_2$ (a)
Fmoc-Leu-Ser(Bu^t)-Thr(Bu^t)-Cys(SBu^t)-Val-Leu-OCH$_2$-phenyl-(p)OCH$_2$-co(polystyrene-1%-divinyl-benzene)

1 g of p-hydroxymethyl-phenoxymethyl-co(polystyrene-1%-divinyl-benzene) is left to swell in dimethylformamide/methylene chloride 1:4 (v/v), filtered and mixed with a solution of 0.74 g of Fmoc-Leucine and 0.19 g of 1-hydroxybenzotriazole in 5 ml of the above-mentioned solvent mixture. Then, 0.43 g of dicyclohexylcarbodiimide and 85 mg of 4-dimethylaminopyridine, each in 5 ml of the same solvent mixture, are added.

The mixture is stirred for 16 hours at 20°, filtered, and washed with the solvent mixture and then with dimethylformamide. Fmoc-Leu-OCH$_2$-phenyl-(p)-OCH$_2$-co(polystyrene-1%-divinylbenzene) is obtained. After splitting off the Fmoc group by means of treatment (10 minutes) with piperidine/dimethylformamide (1:4, v/v) and washing with dimethylformamide, the following reagents, each in 5 ml of dimethylformamide, are added: 0.71 g of Fmoc-valine, 0.28 g of 1-hydroxybenzotriazole and 0.32 ml of diisopropylcarbodiimide, and the mixture is stirred for ¾ hours. The same reactions (splitting of the Fmoc group, coupling of the next Fmoc-amino acid) are effected in sequence: Fmoc-Cys(SBu^t)-OH (0.9 g), Fmoc-Thr(Bu^t)-OH (0.83 g), Fmoc-Ser(Bu^t)-OH (0.8 g) and Fmoc-Leu-OH (0.74 g). After each coupling process, a check is made using a ninhydrin test that coupling has been complete.

The title compound is obtained.

(b) Fmoc-Leu-Ser-Thr-Cys(SBu^t)-Val-Leu-OH 1.2 g of Fmoc-Leu-Ser(Bu^t)-Thr(Bu^t)-Cys(SBu^t)-Val-Leu-OCH$_2$-phenyl-OCH$_2$-co(polystyrene-1%-divinzylbenzene) (ca. 0.4 mmol peptide/g) are stirred for 1 hour in 10 ml of trifluoroacetic acid/methylene chloride 1:1 (v/v). The mixture is filtered, residual resin is washed with trifluoroacetic acid/methylene chloride 1:1, then with methylene chloride, the filtrate is concentrated under vacuum, and precipitated with 25 ml of ether. The deposit is washed with ether and vacuum dried. The title compound is obtained.

(c)
Fmoc-Leu-Ser-Thr-Cys(SBu^t)-Val-Leu-Gly-Lys(Boc)-Leu-Ser-Gln-Glu(OBu^t)-Leu-His-Lys(Boc)-Leu-Gln-Thr-Tyr-Pro-Arg-Thr-Asn-Thr-Gly-Ser-Gly-Thr-Pro-NH$_2$ 1.0 g of the product of stage b is dissolved in 15 ml of dimethylformamide, then 2.3 g of H-Gly-Lys(Boc)-Leu-Ser-Gln-Glu(OBu^t)-Leu-His-Lys(Boc)-Leu-Gln-Thr-Tyr-Pro-Arg-Thr-Asn-Thr-Gly-Ser-Gly-Thr-Pro-NH$_2$, 0.33 g of 3,4-dihydro-3-hydroxy-4-oxo-1,2,3-benzotriazine and 0.31 g of dicyclohexylcarbodiimide are added, and the mixture is stirred for 16 hours at 25°. The mixture is filtered, the filtrate is evaporated to dryness, the residue is washed with diethylether, chloroform, acetone, vacuum dried and the title compound is obtained.

(d)
H-Leu-Ser-Thr-Cys(SBu^t)-Val-Leu-Gly-Lys(Boc)-Leu-Ser-Gln-Glu(OBu^t)-Leu-His-Lys(Boc)-Leu-Gln-Thr-Tyr-Pro-Arg-Thr-Asn-Thr-Gly-Ser-Gly-Thr-Pro-NH$_2$, acetate 0.8 g of the protected peptide of stage (c) are dissolved in 8 ml of piperidine/dimethylformamide 1:4 (v/v), and stirred for 10 minutes. After evaporation under reduced pressure at 25°, the residue is dissolved in 4 ml of dimethylformamide. 50 μl of glacial acetate acid are added, and the solution is poured into 80 ml of ether. The precipitated product is filtered off by suction, washed with ether and vacuum dried at 20°. The title compound is obtained.

(e)
H-Leu-Ser-Thr-Cys(H)-Val-Leu-Gly-Lys(Boc)-Leu-Ser-Gln-Glu-(OBu^t)-Leu-His-Lys(Boc)-Leu-Gln-Thr-Tyr-Pro-Arg-Thr-Asn-Thr-Gly-Ser-Gly-Thr-Pro-NH$_2$, acetate 0.46 g of the peptide of stage (d) are dissolved in 2.5 ml of trifluoroethanol, and mixed under argon with 0.69 ml of tributylphosphine. The solution is stirred for 30 minutes at 20°, then poured, still under argon, into 50 ml of ethyl acetate, and centrifuged. The deposit is suspended in ethyl acetate and again centrifuged. The moist residue (title compound) is used as such immediately in the next reaction.

(f) Boc-Cys(Scm)-OH, dicyclohexylammonium salt

A solution, cooled to −5°, of 1.39 g of Boc-Cys(Trt)-OH in 15 ml of chloroform/methanol 2:1 (v/v) is mixed with 0.5 ml of methoxycarbonylsulphenyl chloride and 0.31 ml of diethylamine, and stirred for 1 hour at the same temperature. 0.33 ml of diethylamine are added, and the solution is stirred for a further 5 minutes at 0°, diluted with 50 ml of chloroform, washed with 10% phosphoric acid, water, and dried over magnesium sulphate. After evaporation of the solvent, the yellow oil is dissolved in 3 ml of ether and mixed with 0.6 ml of dicyclohexylamine at +4°. The crystalline mass is filtered off by suction, washed with ether and dried under a high vacuum at 30°. The title compound is obtained.

M.p. 142°-143° C. $[\alpha]_D^{20} = -31°$ (c=1 in dimethylformamide).

(g)

H—Leu—Ser—Thr—Cys(Boc—Cys—OH)—Val—Leu—Gly—

—Lys(Boc)—Leu—Ser—Gln—Glu(OBu^t)—Leu—His—

—Lys(Boc)—Leu—Gln—Thr—Tyr—Pro—Arg—Thr—Asn—

—Thr—Gly—Ser—Gly—Thr—Pro—NH$_2$, acetate

The peptide of stage (e) is dissolved under argon in 6 ml of trifluoroethanol, and mixed with a solution of 0.16 g of Boc-Cys(Scm)-OH.dicyclohexylammonium salt in 65 ml of trifluoroethanol. The solution is stirred for 2 hour under argon, concentrated under vacuum to ca. 7 ml, and poured into 50 ml of ether. The deposit is filtered off by suction, washed with ether and vacuum dried at 25°.

The title compound is obtained.

(h)

H—Leu—Ser—Thr—Cys(H—Cys—OH)—Val—Leu—Gly—

—Lys—Leu—Ser—Gln—Glu—Leu—His—Lys—Leu—Gln—

—Thr—Tyr—Pro—Arg—Thr—Asn—Thr—Gly—Ser—Gly—

—Thr—Pro—NH₂

3.0 g of the protected peptide of stage (g) are dissolved under a nitrogen atmosphere in 100 ml of trifluoroacetic acid, left to stand for 15 minutes at 20° and evaporated to dryness. The product is purified by "reversed-phase" chromatography (gradient of acetonitrile in water/trifluoroacetic acid) on octadecyl silica. The fractions containing the pure product are combined and evaporated to dryness. The product is filtered over a basic ion exchanger in acetate form, and the filtrate is lyophilised. The title compound is obtained as polyacetate, polyhydrate.

$[\alpha]_D^{20} = -42+$ (in 95% acetic acid, c=0.3). F=0.86.

EXAMPLE 2

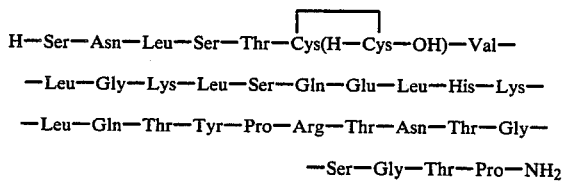

—Ser—Gly—Thr—Pro—NH₂

(a) Boc-Cys(Acm)-Val-Leu-OMe 28.1 g of HCl.H-Val-Leu-OMe, 29.2 g of Boc-Cys-(Acm)-OH, and 13.6 g of 1-hydroxybenzotriazole are dissolved in 200 ml of methylene chloride, cooled to 5°, then 21.0 g of dicyclohexylcarbodiimide and 10.1 ml of N-methylmorpholine are added, and the solution is stirred for 2 hours, during which time the temperature is allowed to rise to 20°. The mixture is filtered, the filtrate is evaporated to dryness, the residue taken up in ethyl acetate and washed with 10% phosphoric acid, water, 1N NaHCO₃ and water. The organic phase is dried over sodium sulphate and evaporated to give the title compound.

(b) H-Thr-Cys(Acm)-Val-Leu-OH 20.8 g of Boc-Cys(Acm)-Val-Leu-OMe are dissolved in 120 ml of trifluoroacetic acid. After 40 minutes, the solution is evaporated to dryness, the residue dissolved in methanol and the solution filtered over a slightly basic ion exchanger resin. The filtrate is evaporated to dryness. The residue is dissolved in tetrahydrofuran, mixed with 8.8 g of Boc-Thr-OH and 5.4 g of 1-hydroxybenzotriazole, and after cooling to 0°, with 8.4 g of dicyclohexylcarbodiimide. The mixture is stirred for 2 hours at 20°, filtered, evaporated to dryness, and then the residue is dissolved in ethyl acetate, washed with 10% phosphoric acid, water, 1N NaHCO₃ and water, dried over Na₂SO₄ and evaporated. The residue is dissolved in 150 ml of trifluoroacetic acid and after 40 minutes, evaporated at reduced pressure, triturated with ether and dried. The residue is dissolved in 200 ml of methanol and treated with 45 ml of 1N NaOH. After one hour, 100 ml of water are added, methanol is removed under reduced pressure, and the aqueous solution is filtered over a weakly acid ion exchange-resin. The filtrate is evaporated to dryness and the title compound is obtained.

(c) Boc-Ser-Asn-Leu-Ser-NHNH₂

17 g of Boc-Ser-Asn-Leu-Ser-OMe are dissolved in 200 ml of hydrazine hydrate, stirred for 2 hours at 20°, and evaporated to dryness at 25°. The residue is washed with diethylether, dried, and the title compound is obtained.

(d) Boc-Ser-Asn-Leu-Ser-Thr-Cys(Acm)-Val-Leu-OH 13.6 g of Boc-Ser-Asn-Leu-Ser-NHNH₂ are dissolved in 150 ml of dimethylformamide, cooled to −20°, then 40 ml of an anhydrous solution of HCl (2N) in dioxane are added, followed by 3.6 ml of tert.-butylnitrite. After 10 minutes at −20°, 16 ml of triethylamine and 13.0 g of H-Thr-Cys(Acm)-Val-Leu-OH are added, and the solution stirred for 16 hours at 25°. The mixture is filtered, the filtrate is evaporated to dryness, the residue is suspended repeatedly in 1N acetic acid and in water, filtered and dried to give the title compound.

(e) Boc-Ser-Asn-Leu-Ser-Thr-Cys(Acm)-Val-Leu-Gly-Lys(Boc)-Leu-Ser-Gln-Glu(OBuᵗ)-Leu-His-Lys(Boc)-Leu-Gln-Thr-Tyr-Pro-Arg-Thr-Asn-Thr-Gly-Ser-Gly-Thr-Pro-NH₂

1.0 g of the product of stage (d) is dissolved in 15 ml of dimethylformamide, to which 2.3 g of H-Gly-Lys(-Boc)-Leu-Ser-Gln-Glu-(OBuᵗ)-Leu-His-Lys(Boc)-Leu-Gln-Thr-Tyr-Pro-Arg-Thr-Asn-Thr-Gly-Ser-Gly-Thr-Pro-NH₂, 0.33 g of 3,4-dihydro-3-hydroxy-4-oxo-1,2,3-benzotriazine and 0.31 g of dicyclohexylcarbodiimide are added, and stirred for 16 hours at 25°. The mixture is filtered, the filtrate evaporated to dryness, the residue washed with diethylether, chloroform, acetone, and the title compound is obtained.

(f)

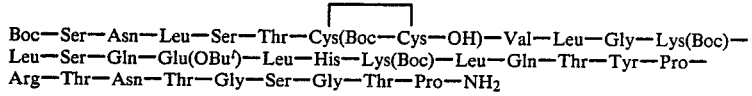

The product of stage (e) is dissolved in 100 ml of chloroform/methanol 1:1. 0.18 ml of methoxycarbonylsulphenyl chloride are added at 0° and the mixture stirred for 1½ hours at this temperature. Then, 0.20 ml of diethylamine are added. After 5 minutes at 0°, 0.3 g Boc-cysteine are added and stirred for a further 2 hours at room temperature. The solution is concentrated under reduced pressure, the product is precipitated with diethylether, filtered off by suction and dried. The title compound is obtained.

(g)

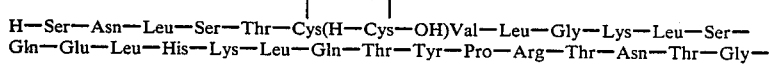

Ser—Gly—Thr—Pro—NH₂

3.0 g of the product of stage (f) are dissolved under a nitrogen atmosphere in 100 ml of trifluoroacetic acid, left to stand for 15 minutes at 20° and evaporated to dryness.

The product is purified by "reversed-phase" chromatography (gradient of acetonitrile in water/trifluoroacetic acid). The fractions containing the pure product are combined and evaporated to dryness. The product is filtered over a basic ion exchanger in acetate form, and the filtrate is lyophilised. The title compound is obtained in polyacetate, polyhydrate.

$[\alpha]_D^{20} = -62°$ (in 50% acetic acid, c=0.19), or $[\alpha]_D^{20} = -64.2$ (in 50% acetic acid; c=0.31). F=0.80.

EXAMPLE 3

Nᵅ-Isocaproyl-Ser-Thr-Ala-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro-NH₂

(a)

Nᵅ-Isocaproyl-Ser(Buᵗ)-Thr(Buᵗ)-Ala-Val-Leu-OCH₂-phenyl-(p)OCH₂-co-(polystyrene-1%-divinylbenzene)

The Nᵅ-Fmoc protecting groups removed from Fmoc-Leu-OCH₂-phenyl-(p)OCH₂-co(polystyrene-1%-divinylbenzene) (1.56 g corresponding to 0.7 mMol) by treating with piperidine (20% v/v) in DMF for 10 minutes and the resin washed with DMF. To the resin is added, in 5 ml of DMF, 0.71 g Fmoc-Val-OH, 0.28 g 1-hydroxybenzotriazole and 0.32 ml diisopropylcarbodiimide. After 45 minutes, the mixture is filtered and the resin washed with DMF. The cycle-removal of the Fmoc-group and coupling of the amino acid- is repeated with, in succession: Fmoc-Ala-OH (0.65 g), Fmoc-Thr (Buᵗ)-OH (0.38 g) and Fmoc-Ser (Buᵗ)-OH (0.8 g).

In the next reaction cycle the amino acid derivative is replaced by isocaproic acid (0.41 g), and 0.53 g 1-hydroxybenzotriazole, and 0.54 g diisopropylcarbodiimide are used over 15 hours. The resin is washed well with DMF and methylene chloride, dried in a vacuum at 40° C. over 15 hours and the protected peptide resin is obtained as a colourless powder.

(b) Nᵅ-Isocaproyl-Ser-Thr-Ala-Val-Leu-OH

Nᵅ-Isocaproyl-Ser(Buᵗ)-Thr(Buᵗ)-Ala-Val-Leu-OCH₂-phenyl-(p)OCH₂-co(polystyrene-1%-divinylbenzene) (1.0 g) is stirred in a mixture of trifluoroacetic acid (5 ml) and methylene chloride (5 ml). The reaction mixture is filtered, the resin washed with the same mixture (5 ml), then with methylene chloride, concentrated under reduced pressure and the product completely precipitated with ether.

The precipitate is filtered off, washed well with ether and dried under reduced pressure over solid potassium hydroxide. The title compound is obtained as a colourless amorphous powder.

(c)

Nᵅ-Isocaproyl-Ser-Thr-Ala-Val-Leu-Gly-Lys(Boc)-Leu-Ser-Gln-Glu(OBuᵗ)-Leu-His-Lys(Boc)-Leu-Gln-Thr-Tyr-Pro-Arg-Thr-Asn-Thr-Gly-Ser-Gly-Thr-Pro-NH₂

To a solution of Nᵅ-isocaproyl-Ser-Thr-Ala-Val-Leu-OH (0.165 g) in DMF (7 ml) is added H-Gly-Lys(-Boc)-Leu-Ser-Gln-Glu(OBuᵗ)-Leu-His-Lys(Boc)-Leu-Gln-Thr-Tyr-Pro-Arg-Thr-Asn-Thr-Gly-Ser-Gly-Thr-Pro-NH₂ hydrochloride (0.59 g), 3,4-dihydro-3-hydroxy-4-oxo-1,2,3-benzotriazine (0.017 g), dicyclohexylcarbodiimide (0.065 g) then N-ethyl-N-N-diisopropylamine until the mixture showns a reaction of pH 6 on wet pH paper. After 16 hours the title compound is precipitated by the addition of ether and dried.

(d)

Nᵅ-Isocaproyl-Ser-Thr-Ala-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro-NH₂

0.5 g of the product from step (c) is dissolved in a mixture of trifluoroacetic acid (50% v/v) and methylene chloride. After 1 hour 50 ml ether (containing 0.6 mMol HCl) are added. The product is filtered off, washed with ether and dried in a vacuum. The product is purified through reversed phase chromatography in a gradient of acetonitrile in phosphoric acid (2%). The fractions containing the pure substance are combined and filtered over a basic ion exchange column in the acetate form.

The title compound is lyophilized and is obtained in the form of an polyacetate, polyhydrate.

$[\alpha]_D^{20} = -32.2°$ (c=0,3 in AcOH 95%). F=0.87.

In analogous manner to the examples 1, 2 or 3 the following compounds of formula I are produced:
(a) of formula A-Leu-Ser-Thr-A₇-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-ProNH₂.

| Ex. | A | A₇ | F | $[\alpha]_D^{20}$ |
|---|---|---|---|---|
| 4 | H—Ser—Asn— | Cys | 0.79 | −40.0° (c = 0.32 in AcOH 50%) |
| 5 | H—Ser—Asn— | Cys(—S—CH₂—CH₂—COOH)[1] | | −52.8° (c = 0.4 in AcOH 50%) |
| 6 | H—Ser—Asn— | Asu | 0.78 | −20° (c = 0.4 in AcOH 95%) |
| 7 | H—Asn— | Cys(H — Cys—OH) | 0.77 | −15° (c = 0.4 in AcOH 100%) |
| 8 | H—Ser—Asn | Glu | 0.70 | −21.5° (c = 0.4 in AcOH 95%) |
| 9 | H—Ser—Asn— | Ala | 0.81 | −25.2° (c = 0.23 in AcOH 95%) |
| 10 | H—Ser—Asn— | Ser | 0.77 | −26.3° (c = 0.4 in AcOH 95%) |
| 11 | H—Gly—Asn— | Cys(H — Cys—OH) | 0.83 | −41.8° (c = 0.28 in AcOH 95%) |
| 12 | H—Ser—Asn— | Cys(Me) | 0.80 | −27.7° (c = 0.26 in AcOH 95%) |

-continued

| Ex. | A | A7 | F | $[\alpha]_D^{20}$ |
|---|---|---|---|---|
| 13 | H—Ser— | Cys(H—Cys—OH) | 0.85 | −31.6° (c = 0.38 in AcOH 85%) |
| 14 | H— | Ala | 0.91 | −30.4° (c = 0.44 in AcOH 95%) |
| 15 | H—Ser—Asn— | Cys(Acm) | 0.78 | −21° (c = 0.16 in AcOH 95%) |
| 16 | H—Ser—Asn— | Lys | 0.78 | −21.7° (c = 0.41 in AcOH 95%) |
| 17 | H—Ser—Asn— | Arg | 0.86 | −24.2° (c = 0.33 in AcOH 95%) |
| 18 | H— | D-Ala | 0.90 | −26.5° (c = 0.62 in AcOH 95%) |
| 19 | CH₃CO— | Ala | 0.90 | −34.7° (c = 0.34 in AcOH 95%) |
| 20 | H— | Phe | 0.83 | −30.0° (c = 0.43 in AcOH 95%) |

¹F = 0.77

(b) of formula A-Thr-A7-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-ProNH₂

| Ex. | A | A7 | $[\alpha]_D^{20}$ (c in AcOH 95%) | F |
|---|---|---|---|---|
| 21 | H—Ser—Asn—Ser | Cys(H—Cys—OH) | −36.8° (0.47) | 0.79 |
| 22 | H—Ser | Cys(H—Cys—OH) | −44.2° (0.59) | 0.85 |
| 23 | H—Ser—Asn—Leu | Cys(H—Cys—OH) | −34.9° (0.3) | 0.82 |
| 24 | H—Ser—Leu | Cys(H—Cys—OH) | −34.4° (0.27) | 0.85 |
| 25 | H—Leu—DAla | Ala | −27.7° (0.53) | 0.90 |
| 26 | H—DLeu—Ser | Ala | −31.3° (0.47) | 0.83 |
| 27 | H—Phe—Ser | Ala | −33.9° (0.52) | 0.90 |
| 28 | H—Leu—DSer | Ala | −26.4° (0.28) | 0.84 |
| 29 | Adamantanacetyl—Ser | Ala | −30.5° (0.4) | 0.83 |
| 30 | H—Leu—Ala | Ala | −31.7° (0.32) | 0.90 |
| 31 | H—Leu | Ala | −35.4° (0.35) | 0.86 |
| 32 | H—Cha—Ser | Ala | −26.2° (0.45) | 0.85 |
| 33 | CH₃CO—Ser | Ala | −33.3° (0.37) | 0.92 |
| 34 | H—Ala—Ser | Ala | −32.0° (0.50) | 0.90 |
| 35 | H—Pro—Ser | Ala | −37.5° (0.44) | 0.86 |
| 36 | Cyclohexylpropionyl—Ser | Ala | −28.3° (0.24) | 0.83 |
| 37 | Cyclopentyl—CO—Ser | Ala | −35.1° (0.37) | 0.90 |
| 37a | Pyroglutamoyl—Ser | Ala | −34.6 (0.3) | 0.87 |
| 37b | Decanoyl—Ser | Ala | −25.6 (0.25) | 0.91 |

(c) of formula H-Leu-Ser-A6-Ala-A8-A9-Gly-Lys-Leu-Ser-Gln-Glu-Leu-His-Lys-Leu-Gln-Thr-Tyr-Pro-Arg-Thr-Asn-Thr-Gly-Ser-Gly Thr-ProNH₂

| Bsp. | A6 | A8 | A9 | $[\alpha]_D^{20}$ | c in AcOH 95% | F |
|---|---|---|---|---|---|---|
| 38 | Thr | Gly | Leu | −25.3° | (0.43) | 0.85 |
| 39 | Thr | Val | DLeu | −26.9° | (0.51) | 0.86 |
| 40 | DThr | Val | Leu | −17.6° | (0.55) | 0.85 |
| 41 | Thr | Val | Phe | −28.6° | (0.44) | 0.88 |
| 42 | Thr | Aib | Leu | −28.0° | (0.50) | 0.88 |

EXAMPLE 43

H-Gly-Asn-Leu-Ser-Thr-Cys(H-Cys-OH)-Nle-Leu-Gly-Thr-Tyr-Thr-Gln-Asp-Phe-Asn-Lys-Phe-His-Thr-Phe-Pro-Gln-Thr-Ala-Ile-Gly-Val-Gly-Ala-Pro-NH₂

Produced in analogy to Example 2.
$[\alpha]_D^{20} = -44°$ (c=0.11 in AcOH 95%). (F=0.75).

EXAMPLE 44

N$^\alpha$-Isoeaproyl-Ser-Thr-Ala-Val-Leu-Gly-Lys-Leu-Ser-Gln-Glu-Leu-His-Lys-Leu-Gln-Thr-Tyr-Pro-Arg-Thr-Asp-Val-Gly-Ala-Gly-Thr-Pro-NH₂

This peptide is assembled in a stepwise manner on a polystyrene-based resin support. The Boc-group is used for protection of the alpha amino-groups and side-chain functional groups are protected as Lys(2-chlorobenzyloxycarbonyl), Ser(benzyl), Thr(benzyl), Arg(tosyl), His(tosyl), Tyr(4-chlorobenzyloxycarbonyl), Cys(4-methylbenzyl), Glu(benzyl).

Amino-4-methylphenyl-methyl-co(polystyrene-divinylbenzene) resin (0.7 mmol/g) is subjected to the following cycle, steps (1) to (7), of treatments:
(1) DCM
(2) trifluoroacetic acid (50%) in DCM
(3) DCM
(4) diisopropylethylamine (10%) in DMF
(5) DMF
(6) preformed symmetrical anhydride (2,8 mmol per g starting resin) of Boc-amino acid in DMF
(7) DMF Volumes of washes and reagents are 5 to 20 ml per gram of starting resin.

Each step is repeated as many times as necessary for either complete reaction of the resin (steps 2, 4, 6) or complete displacement of the previous reagent from the resin (steps 1, 3, 5, 7). Samples of resin are taken after each cycle and checked for completeness of reaction by a ninhydrin-test.

Symmetrical anhydrides of Boc-amino acids are formed just prior to use by reacting Boc-amino acid (2.8 mmol per g resin) and DCCI (1,4 mmol per g resin) in DCM, containing DMF in amounts sufficient for complete dissolution of the Boc-amino acid. The mixture is filtered, more DMF added to the filtrate, the volume is reduced by evaporation of DCM at a temperature not exceeding 15° C. and the resulting solution is used in step (6).

The cycle of reactions (1) to (7) is repeated for the amino acid residues such as to provide the sequence of formula I, except for Boc-Gln-OH and Boc-Arg(Tos)-OH which are coupled in step (6) as their preformed 1-hydroxybenzotriazole esters in DMF.

In the last cycle, in step (6), isocaproic acid, diisopropylcarbodiimid and 1-'hydroxybenzotriazol (all at 3.5 mmol per g of starting resin) in DMF are added to the resin. After 15 hours, the resin is washed with DMF and DCM and dried.

To the peptide resin (1 g) are added p-cresol (1 g), dimethylsulfide (1 ml) and HF (10 ml). After 1 hour at 0° C., the volatile components are destilled off at 0° C. The residue is washed with ethylacetate and extracted with several portions of acetic acid (10%) in water and the aqueous extract lyophilized. The lyophilized product is purified by "reversed-phase chromatography on a column of octadecyl-silica which is eluted with a gradient of acetonitril in phosphoric acid (2%). Fractions containing the compound in pure form are combined, filtered through a weakbase ion-exchange resin in the acetate form, lyophilized and dried. The title-compound is obtained as a white, fluffy powder $[\alpha]_D^{20} = -34.0$ (c=0.53 in acetic acid). F=0.93.

The compounds of formula I as well as their pharmaceutically acceptable salts and complexes exhibit valuable pharmacological properties as indicated in animal tests. They are therefore useful as pharmaceuticals.

In particular they lower the calcium plasma level and antagonise the parathormone to give a positive calcium balance in bones.

The hypocalcemic effect of the compounds may be observed in conventional manner, for example according to the method of M. Azria et al reported in Calcitonin 1984 Symposium 2–4th October, Milan published in 1986 as Short Communications in the Current Clinical Practice Series No. 42, Excerpta Medica 1986, p. 104.

In this method a calcium [2+]ion selective electrode is used to measure continuously the calcium ion content in blood of rabbits. The compounds are administered s.c. at a dose of from 0.1 to about 10 microgram/kg, e.g. corresponding to 1 I.U. per kg. The measurements are effected over 5 hours and the area under the curve measured.

The compounds can also be tested in other tests, e.g. the standard hypocalcemic test of M. Kumar et al, J. Endocrinology, (1965), 33, p. 469 in rats at the same doses. Hypocalcemic activity of 300 to 6000 I.U. per milligram is obtained in this test.

Examples 3, 29 and 36 are the preferred compounds.

The compounds of formula I are thus useful for all conditions in which it is desirable to reduce the plasma calcium level or to influence bone metabolism, e.g. hypercalcaemia as a result of endogenic thyrocalcitonin deficiency through loss of thyroid tissue or hyperfunction of the parathyroid. They are also indicated for all bone conditions which are associated with increased degradation or in which calcium fixation in the bones is desirable, e.g. osteoporosis of various causes (e.g. post-climacteric, post-traumatic, caused by cortico-steroid therapy or inactivity, for malignant illnesses etc.), fractures, osteo-malacia, rickets and renally-induced osteodystrophy, pain e.g. bone pain associated with osteoporosis, neurodystrophic diseases, Paget's disease, as well as in particular for combined therapy with calcium or phosphate.

The compounds according to the invention also inhibit pancreas secretion. This indication may be shown in animals, e.g. using the method described in Scand. J. Gastroint. 6, (1975) by S. J. Konturek et al, at the same dosages indicated above.

The compounds according to the invention are therefore further useful in acute pancreatitis, and gastrointestinal disorders such as ulcers.

For all these indications, the exact dosage will of course vary depending upon the compound employed, mode of administration and treatment desired.

In general, satisfactory results are obtained when administered at a daily dosage of from about 0.1 to 20 I.U. per kilogram. For the larger mammals as indicated daily dosage is in the range from about 5 to about 1500 I.U., e.g. 50 to 200 I.U., e.g. corresponding to about 0.01 to about 0.7 milligrams.

The indicated daily dose is conveniently administered in unit dosage form, once-a-day or if desired once every two or three days in daily doses of from about 5 to about 1500 I.U.

The compounds may be administered in free form, or in pharmaceutically acceptable salt form or complex form. These forms have the same order of activity. A pharmaceutically composition comprises a compound of formula I in free form or in pharmacologically acceptable salt or complex form in association with a liquid or solid carrier. The pharmaceutical compositions may be prepared in conventional manner and may for example be for intramuscular injection or nasal administration. The formulation may be a depot formulation.

The present invention also provides in another aspect a compound of formula I in free form or in pharmaceutically acceptable acid or complex form for use as for inducing a hypocalcemic effect, or treating Paget's disease, or osteoporosis, bone pain associated therewith, a neurodystrophic disorder, or pancreatis (including all the indications mentioned above).

The compounds of the invention may be administered in similar manner to known standards for use in these indications for example salmon calcitonin.

The suitable daily dosage for a particular compound will depend on a number of factors such as its relative potency of activity. It has for example been determined that the preferred compound of the invention, i.e. the compounds of Examples 3, 29 and 36 have 137, 120 and 123 percent of the activity of salmon calcitonin in the hypocalcemic test of M. Azria et al. In the Kumar test the compounds of Examples 2, 3 and 5 had similar activities to that of salmon calcitonin. It is therefore indicated that the compound may be administered at similar or lower dosages than conventionally employed for salmon calcitonin.

What we claim is:

1. A compound of the formula:

$$R-(NH-\overset{Y_1}{\underset{|}{CH}}-CO)_n-A_6-NH-\overset{Y_2}{\underset{|}{CH}}-CO-A_8-A_9-Z-ProNH_2 \quad I$$

wherein
R is H or R'CO and
$R_1$ is
  (a) a $(C_{1-17})$alkyl radical,
  (b) $(C_{5-7})$cycloalkyl or $(C_{5-7})$cycloalkyl$(C_{1-2})$-alkyl radicals;
  (c) Adamantyl, adamantylmethyl or adamantylethyl; or
  (d) pheyl, benzyl, phenylethyl, or 5-oxo-2-pyrrolidinyl,
$Y_1$ is the radical linked to an alpha carbon atom of Leu, Asn, Pro, Ser, Phe, D-Leu, Gly, Ala, cyclohexylalanine or α-aminoisobutyric acid,
$Y_2$ is the radical linked to an alpha carbon atom of Cys, Ala, Glu, Ser, Lys, Arg, Phe, $$-CH_2-S-S-CH_2-\underset{\underset{NH_2}{|}}{Ch}-COOH,$$

$-CH_2-S-S-CH_2-CH_2-COOH$, $-(CH_2)_p-COOH$ or $-CH_2-S-Y_3$,
$Y_3$ is $(C_{1-4})$alkyl or benzyl optionally substituted by methyl or methoxy, or $CH_3CO-NH-CH_2-$,
n is 1 to 4,
$A_6$ is Thr or D-Thr,
p is 3 to 5,
$A_8$ is the aminoacyl radical of Nle, Val, Gly, or Aib,
$A_9$ is the aminoacyl radical of Leu of Phe,
Z is a polypeptide radical of the formula
  (a)  Gly-Thr-Tyr-Thr-Gln-Asp-Phe-Asn-Lys-Phe-His-Thr-Phe-Pro-Gln-Thr-Ala-Ile-Gly-Val-Gly-Ala
  (b)  Gly-Lys-Leu-Ser-Gln-Glu-Leu-His-Lys-Leu-Gln-Thr-Tyr-Pro-Arg-Thr-Asp-Val-Gly-Ala-Gly-Thr
  (c)  Gly-Lys-Leu-Ser-Gln-Glu-Leu-His-Lys-Leu-Gln-Thr-Tyr-Pro-Arg-Thr-Asn-Thr-Gly-Ser-Gly-Thr.

wherein, when there is more than one $Y_1$ radical, these are the same or different, and, the amino acid moieties $A_6$, $A_8$, $A_9$ and the amino acid moieties defined by $Y_1$ and $Y_2$ can independently be in the D-or L-configuration, in free form, salt form or complex form.

2. A compound of claim 1 wherein $$-NH-\overset{Y_2}{\underset{|}{CH}}-CO-$$

is Ala.

3. A compound of claim 1 wherein n is 2 and R is H or R'CO or n is and R is R'CO.

4. A compound of claim 1 as a hydrate.

5. The compound according to claim 1 which is

H—Gly—Asn—Leu—Ser—Thr—Cys(H—Cys—OH)—Nle—Leu—Gly—Thr—Tyr—Thr—Gln—Asp—Phe—Asn—Lys—Phe—His—Thr—Phe—Pro—Gln—Thr—Ala—Ile—Gly—Val—Gly—Ala—Pro—NH₂ in free form or in salt form or in complex form.

6. A compound according to claim 1 having the formula

A—Leu—Ser—Thr—A₇—Val—Leu—Gly—Lys—Leu—Ser—Gln—Glu—Leu—His—Lys—Leu—Gln—Thr—Tyr—Pro—Arg—Thr—Asn—Thr—Gly—Ser—Gly—Thr—ProNH₂ where A and A₇ are

|     | A                       | A₇                              |
|-----|-------------------------|---------------------------------|
| (a) | H—Ser—Asn—              | Cys                             |
| (b) | H—Ser—Asn—              | Cys(—S—CH₂—CH₂—COOH             |
| (c) | H—Ser—Asn—              | Asu                             |
| (d) | H—Asn—                  | Cys(H — Cys—OH)                 |
| (e) | H—Ser—Asn               | Glu                             |
| (f) | H—Ser—Asn—              | Ala                             |
| (g) | H—Ser—Asn—              | Ser                             |
| (h) | H—Gly—Asn—              | Cys(H — Cys—OH)                 |
| (i) | H—Ser—Asn—              | Cys(Me)                         |
| (j) | H—Ser—                  | Cys(H — Cys—OH)                 |
| (k) | H—                      | Ala                             |
| (l) | H—Cha—Ser               | Ala                             |
| (m) | CH₃CO—Ser               | Ala                             |
| (n) | H—Ala—Ser               | Ala                             |
| (o) | H—Pro—Ser               | Ala                             |
| (p) | Cyclohexylpropionyl—Ser | Ala                             |
| (q) | Cyclopentyl—CO—Ser      | Ala                             |
| (r) | Pyroglutamoyl—Ser       | Ala                             |
| (s) | Decanoyl—Ser            | Ala                             | in free form or in salt form or in complex form.

7. A compound according to claim 1 having the formula

A—Thr—A₇—Val—Leu—Gly—Lys—Leu—Ser—Gln—Glu—Leu—His—Lys—Leu—Gln—Thr—Tyr—Pro—Arg—Thr—Asn—Thr—Gly—Ser—Gly—Thr—ProNH₂ where A and A₇ are

|     | A                    | A₇                       |
|-----|----------------------|--------------------------|
| (a) | H—Ser—Asn—Ser        | Cys(H — Cys—OH)          |
| (b) | H—Ser                | Cys(H — Cys—OH)          |
| (c) | H—Ser—Asn—Leu        | Cys(H — Cys—OH)          |
| (d) | H—Ser—Leu            | Cys(H — Cys—OH)          |
| (e) | H—Leu—DAla           | Ala                      |
| (f) | H—DLeu—Ser           | Ala                      |
| (g) | H—Phe—Ser            | Ala                      |
| (h) | H—Leu—DSer           | Ala                      |
| (i) | Adamantanacetyl—Ser  | Ala                      |
| (j) | H—Leu—Ala            | Ala                      |
| (k) | H—Leu                | Ala                      |
| (l) | H—Ser—Asn—           | Cys(Acm)                 |
| (m) | H—Ser—Asn—           | Lys                      |

-continued

| | A | A₇ |
|---|---|---|
| (n) | H—Ser—Asn— | Arg |
| (o) | H— | D-Ala |
| (p) | CH₃CO— | Ala |
| (q) | H— | Phe | in free form or in salt form or in complex form.

8. A compound according to claim 1 having the formula

H—Leu—Ser—A₆—Ala—A₈—A₉—Gly—Lys—Leu—Ser—Gln—Glu—Leu—His—Lys—Leu—Gln—Thr—Tyr—Pro—Arg—Thr—Asn—Thr—Gly—Ser—Gly—Thr—ProNH₂ where A₆, A₈ and A₉ are

| | A₆ | A₈ | A₉ |
|---|---|---|---|
| (a) | Thr | Gly | Leu |
| (b) | Thr | Val | DLeu |
| (c) | (D)Thr | Val | Leu |
| (d) | Thr | Val | Phe |
| (e) | Thr | Aib | Leu | in free form or in salt form or in complex form.

9. A compound of claim 1 which is

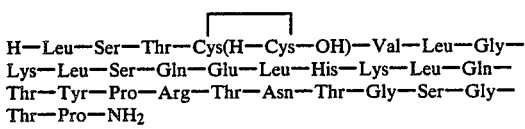
H—Leu—Ser—Thr—Cys(H—Cys—OH)—Val—Leu—Gly—Lys—Leu—Ser—Gln—Glu—Leu—His—Lys—Leu—Gln—Thr—Tyr—Pro—Arg—Thr—Asn—Thr—Gly—Ser—Gly—Thr—Pro—NH₂ in free form or in salt form or complex form.

10. A compound of claim 1 which is

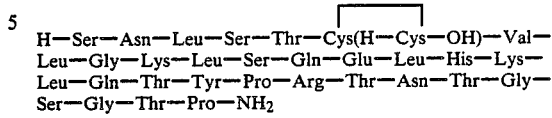
H—Ser—Asn—Leu—Ser—Thr—Cys(H—Cys—OH)—Val—Leu—Gly—Lys—Leu—Ser—Gln—Glu—Leu—His—Lys—Leu—Gln—Thr—Tyr—Pro—Arg—Thr—Asn—Thr—Gly—Ser—Gly—Thr—Pro—NH₂ in free form or in salt form or complex form.

11. A compound of claim 1 which is N^α-Isocaproyl-Ser-Thr-Ala-Val-Leu-Gly-Lys-Leu-Ser-Gln-Glu-Leu-His-Lys-Leu-Gln-Thr-Tyr-Pro-Arg-Thr-Asn-Thr-Gly-Ser-Gly-Thr-Pro-NH₂ in free form, in salt form or in complex form.

12. A compound of claim 1 which is N^α-Isocaproyl-Ser-Thr-Ala-Val-Leu-Gly-Lys-Leu-Ser-Gln-Glu-Leu-His-Lys-Leu-Gln-Thr-Tyr-Pro-Arg-Thr-Asp-Val-Gly-Ala-Gly-Thr-Pro-NH₂ in free form, in salt form or in complex form.

13. A method of treating a subject suffering from hypercalcemia, Paget's disease, or osteoporosis, bone pain associated therewith, a neurodystrophic disorder, pancreatis or gastrointestinal disturbances which comprises administering a compound of claim 1 to an animal in need of such treatment.

14. A pharmaceutical composition useful in treating hypercalcemia, Paget's disease, or osteoporosis, bone pain associated therewith, neurodystrophic disorder, pancreatis or gastrointestinal disturbances comprising a compound of claim 1 in free form or in pharmacologically acceptable salt or complex form in association with a pharmaceutically acceptable liquid or solid carrier.

* * * * *